United States Patent [19]

Raab

[11] 4,365,359
[45] Dec. 28, 1982

[54] PMMA COATED BONE CONNECTIVE PROSTHESES AND METHOD OF FORMING SAME

[76] Inventor: Simon Raab, 5872 Westbury Ave., Montreal, Quebec, Canada, H3W 2W9

[21] Appl. No.: 249,439

[22] Filed: Mar. 31, 1981

Related U.S. Application Data

[63] Continuation-in-part of Ser. No. 45,657, Jun. 5, 1979, Pat. No. 4,281,420.

[30] Foreign Application Priority Data

Feb. 15, 1979 [GB] United Kingdom ............... 7905445

[51] Int. Cl.³ .......................... A61F 1/24; A01N 1/02
[52] U.S. Cl. ........................................ 3/1.912; 3/1.9; 3/1.91; 128/92 C; 128/92 CA; 427/2; 427/388.2; 427/388.5
[58] Field of Search .................................. 3/1.9–1.913; 128/92 C, 92 CA; 433/173–176, 201, 228; 427/2, 388.2, 388.5, 301; 156/332; 134/41

[56] References Cited

U.S. PATENT DOCUMENTS

| | | | |
|---|---|---|---|
| 2,916,469 | 12/1959 | Lal ........................................ | 156/332 |
| 3,078,180 | 2/1963 | Zander et al. ......................... | 134/41 |
| 3,197,340 | 7/1965 | Bellinger .............................. | 134/41 |
| 3,351,504 | 11/1967 | DeHart ............................... | 148/6.14 |
| 3,544,356 | 12/1970 | Vazirani ............................... | 134/41 |
| 3,663,288 | 5/1972 | Miller .................................... | 428/447 |
| 3,713,860 | 1/1973 | Auskern .............................. | 128/92 C |
| 3,790,507 | 2/1974 | Hodosh .............................. | 3/1.91 X |
| 3,907,609 | 9/1975 | Coggins .............................. | 134/41 |
| 3,936,887 | 2/1976 | Hodosh ............................... | 128/92 C |
| 3,938,198 | 2/1976 | Kahn et al. ......................... | 3/1.913 X |
| 3,957,529 | 5/1976 | Alexander et al. ................. | 134/41 X |
| 3,987,499 | 10/1976 | Scharbach et al. ................ | 3/1.9 X |
| 4,065,817 | 1/1978 | Branemark et al. .................. | 3/1.91 |
| 4,234,972 | 11/1980 | Hench et al. ......................... | 3/1.9 |

OTHER PUBLICATIONS

Wittington, "Whittington's Dictionary of Plastics", Technomic Publishing Co., Inc., 1978, pp. 287–288.
Bikales, N. M., Editor, Adhesion and Bonding, John Wiley and Sons, Inc., New York, 1971, pp. 45, 46.
The Knee Joint, Excerpta Medica Amsterdam, American Elsevier Publishing Co., Inc., New York, 1974, Chapter Entitled "Mechanical Properties of Bone Cements In Vitro and Invivo", pp. 1–5.
"Ceramic Implants", Hench L. L., Director of Biomedical Engineering, University of Florida, Gainesville, Florida, 1975.
Park, J. B. et al., Biomat., Med. Dev., Art. Org., 6(4), pp. 361–373, (1978).

*Primary Examiner*—Ronald L. Frinks
*Attorney, Agent, or Firm*—Roylance, Abrams, Berdo & Farley

[57] ABSTRACT

A PMMA film is fixedly adhered to a prosthetic element by applying PMMA to the surface of the prosthetic element in the presence of a silane coupling agent. The resultant prosthesis is adapted to be joined to bone by means of bone cement.

30 Claims, 2 Drawing Figures

PMMA COATED BONE CONNECTIVE PROSTHESES AND METHOD OF FORMING SAME

CROSS-REFERENCE TO RELATED APPLICATION

This application is a continuation-in-part of my copending application Ser. No. 45,657, filed June 5, 1979, now U.S. Pat. No. 4,281,420.

BACKGROUND OF THE INVENTION

1. Field of the Invention

The present invention relates to prostheses adapted to be fixedly attached to bone by means of a bone cement. Specifically, the present invention is directed towards prostheses adapted to maximize the strength and durability of the prostheses/bone cement adherence.

2. Description of the Prior Art

In the field of orthopedic surgery, ZIMALOY, manufactured by Zimmer, U.S.A., Inc., a chromium-cobalt-molybdenum alloy, stainless steel, titanium alloys, and polymerized materials such as ultra high molecular weight polyethylene (hereinafter UHMWPE) have been used successfully to replace the ends of long bones and joints, including the hip joint. However, there exists a severe limitation with respect to such orthopedic surgery, namely, coupling of the protheses to bone. Due to such factors as mechanical stress, fatigue, corrosion, etc., the prostheses/bone cement joints have been prone to failure.

Present methods of utilizing such bone prostheses involve the use of a prosthesis having a stem portion which is inserted into the interior of a bone. A bone cement comprising a mixture of polymethylmethacrylate (hereinafter PMMA) polymer and methyl methacrylate monomer (hereinafter MMA) and optionally including a styrene co-polymer of PMMA is likewise inserted into the bone cavity and is utilized to couple the stem of the implant to the bone itself. Experience has demonstrated, however, that serious drawbacks exist with respect to the coupling between the prosthesis stem and the bone cement. Attempted solutions to this problem have been directed primarily toward strengthening the prosthesis/bone cement interface by means of gross mechanical interlock involving, for example, dove tails, small stems, etc. Such devices result in stress concentrations that can exceed the strength of the bone cement as well as cause non-physiological force distribution in the bone.

Adherence at the interface between the implant and PMMA is greatly restricted by current industrial and surgical practices. For instance, the PMMA cement is typically applied in a highly viscous doughy state with the result that the degree of contact between the implant and the cement is inadequate. Moreover, the existence of weak boundary layers such as contaminants and weak metal oxides on the surface of the implant have also caused problems. Weak boundary layers may be due to the composition of the implant or to the process of forming the same. Thus, in the case of a metal implant, the surface of the implant normally includes weak metal oxides as weak boundary layers. In the case of a polymeric implant, the surface of the implant normally includes a weak boundary layer comprising monomer, partially polymerized or low molecular weight polymer and contaminants comprising mold release agents, etc. Finally, the implant may come in contact with air, blood, water, etc. prior to being inserted into the bone thereby becoming contaminated. The existence of weak boundary layers, e.g., surface contaminants, is detrimental to the formation of good implant-bone cement adherence. Thus, the strength of such joints has been dependent upon gross mechanical interlock. Such difficulties in the formation of a satisfactory prosthesis/bone cement connection have also caused the result that mere resurfacing of a deteriorated joint, e.g., a deteriorated hip joint due to arthritis, was not readily accomplished. Thus, in the case of a deteriorated articular surface, e.g., surface of the head or ball in a ball and socket joint, the entire head of the bone is generally removed and a prosthetic head connected to the bone by means of a stem inserted into the interior of the bone, although in some instances, resurfacing implants have been used with bone cement.

SUMMARY OF THE INVENTION

It has now been discovered that prosthesis fixation problems may be overcome by treating at least that portion of the prosthetic element which is adapted to be connected to bone in order to provide a PMMA film fixedly adhered to said portion. A PMMA film is applied to the prosthetic element in the presence of a silane coupling agent by dipping, painting, spraying, etc.

The resultant prosthesis has a film of PMMA firmly adhered to the surface thereof. This PMMA film adhesively interacts molecularly with PMMA bone cement. Accordingly, the adherence of a prothesis adhesively connected to bone by means of a PMMA cement can be drastically increased.

BRIEF DESCRIPTION OF THE DRAWINGS

In the drawings which form a part of the original disclosure of the present invention.

DETAILED DESCRIPTION OF THE INVENTION

According to the present invention, prostheses exhibiting marked fixation improvements have been discovered. Such a prosthesis comprises a prosthetic element having a PMMA film fixedly adhered to at least a portion of the surface of the prosthetic element. The prothesis includes a surface adapted to be fixedly attached to bone or a bone attachment surface. At least the bone attachment portion of the surface, in accordance with the present invention, is coated with a PMMA film prior to attachment to bone. The PMMA coating or film is adhered to the prosthetic element by a process which comprises applying PMMA to the surface of a prosthetic element in the presence of a silane coupling agent.

Figure 1:
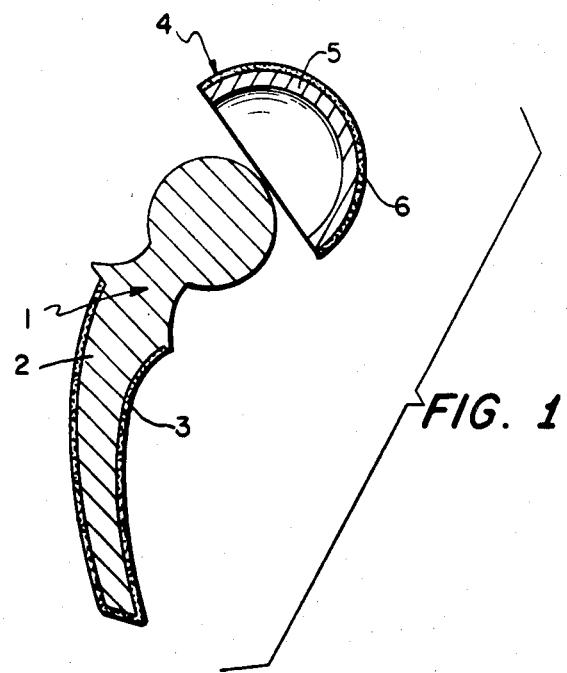
FIG. 1 is an elevational side view in longitudinal section of a PMMA coated hip prothesis prepared in accordance with the present invention.

FIG. 1 is an elevational side view in longitudinal section of a stem insertion hip joint prosthesis having a bone attachment surface bearing a PMMA film. Also shown is a resurfacing prostheses for the socket portion of a hip joint, with the bone attachment surface having a PMMA film fixedly adhered thereto in accordance with the present invention. Thus, in FIG. 1 there is shown a stem insertion prosthesis 1, comprising a rigid prosthetic element 2, which may be composed of a metal alloy or a polymer such as UHMWPE, bearing a thin, high strength PMMA film 3. Also shown is a resurfacing prosthesis 4 for the socket portion of a ball and socket joint, comprising a rigid prosthetic element 5 and a PMMA film 6.

The rigid prosthetic element which is coated in accordance with the present invention may be chosen from any suitable material including metal alloys and plastic. Thus, the element may be composed of a titanium alloy (e.g., Ti-6Al-4V), stainless steel (e.g., SS316LVM), a cobalt-chromium or cobalt-chromium-molybdenum alloy, MP-35 (protozol) or a polymeric material such as ultrahigh molecular weight polyethylene (UHMWPE).

In order to provide a high strength adherent PMMA film in accordance with the present invention, the prosthetic element is preferably first treated to remove any contaminants which may act as weak boundary layers so that the coating may be joined directly to the prosthetic element with no intervening material. In the case of a metal prosthetic element, the weak boundary layer may comprise contaminants such as dirts and oils and additionally typically includes weak metal oxides. In the case of a polymeric prosthetic element, the weak boundary layer typically comprises contaminants such as unreacted monomer, antioxidation agents and mold release agents and additionally low molecular weight polymer.

In the case of a metal prosthetic element, removal of the weak boundary layer may involve a degreasing step. Removal of the weak metal oxides is accomplished by an acid treating step which may be followed by a desmutting and passivation step. However, any treatment which functions effectively to remove contaminants and weak metal oxides may be utilized.

The degreasing treatment may be carried out through the utilization of an aqueous alkaline solution, such as, for example, an aqueous solution of sodium hydroxide. Thus, the prosthetic element to be degreased may be immersed in a 1 N solution of sodium hydroxide which has been heated to its boiling point, for 10 minutes to remove contaminants and grease. Another degreasing treatment which may be utilized with less contaminated elements comprises exposing the prosthetic element to trichloroethylene vapor. In order to determine whether or not degreasing is complete, the "water break test" may be utilized according to which the degreased prosthetic element is rinsed in distilled water. When the element is removed from the water, if the water beads up and runs off in less than 30 seconds, the surface is not clean enough. There should be no break in the film of water nor any tendency of the film to crawl or pucker.

Subsequent to the degreasing treatment, the metallic prosthetic element should preferably be treated with an acid etching treatment in order to remove weakly bound metal oxides. Such treatment may comprise immersing the element in a sulfuric acid/water admixture at an elevated temperature of, for example, 60° C. for a period of approximately ½ hour. Other treatments which may be utilized include immersing the prosthetic element in a sulfuric acid/sodium dichromate aqueous solution or treatment with other acid solutions.

It is preferred that the acid etching treatment be discontinued prior to the accomplishment of any gross surface changes. Thus, it is preferred that the surface which is designed to be attached to bone, be smooth. This results in a more continuous stress concentration about the prosthetic element/bone cement interface. However, where it is desired to use an implant having a rough surface thus promoting a greater degree of mechanical interlock, the coating of the present invention may be utilized and a stronger joint will result.

In the case of an alloy prosthetic element which has been acid etched such as with the sulfuric acid solution discussed above, completion of the etching reaction will be evidenced by a reaction which turns the surface of the element black. This is due to the presence of carbon which is a component of metal alloys. Such presence of carbon indicates that the surface has been sufficiently etched. If no carbon appears, etching is not complete. In order to avoid any gross surface changes, the element should be removed from the etching solution within ten seconds of the appearance of carbon. The etched element may be checked by means of a Hobsyn Tally Surface Profile or an SEM to insure that no gross surface changes have occurred.

Thereafter, any carbon remaining on the surface of the element may be removed by means of a desmutting and passivation treatment. Such desmutting and passivation treatment may be carried out by means of a hydrofluoric acid/nitric acid aqueous admixture heated to an elevated temperature of approximately 60° C. Other strong oxidation reagents may be utilized if desired. When the etched element is immersed in such a solution, there should be a reaction within seconds evidenced by a burst of bubbles as carbon is removed. This is followed by another sudden burst of bubbles evidencing a secondary reaction. At this point, the element should be removed from the desmutting and passivation solution. This treatment functions not only to remove carbon but additionally promotes the formation of a well adhered, uniform, high strength oxide surface, and is a preferred treatment step.

The initial removal of weak boundary layers may be carried out not only by chemical means, i.e., degreasing and acid etching, but mechanical means may be utilized if desired. Thus, the prosthetic element may be treated by blasting with alumina grit to provide a virgin metal surface. Other mechanical treatments such as grinding, honing, machining, etc., may also be utilized.

Following mechanical treatment of the prosthetic element, the treated surface should immediately be immersed in a passivation solution comprising, e.g., nitric and hydrofluoric acid, as above. It is preferred that the passivation treatment be carried out within a short time from the mechanical treatment. The lapse of time between mechanical treatment and passivation should preferably be less than one minute.

Following passivation, the treated element should be rinsed in water until the water has a neutral pH. When the prosthetic element is composed of a Co-Cr-Mo alloy, it is preferred that it be ultrasonically agitated while being rinsed. This removes weakly bound carbide particles which have been exposed in the etching process. These carbides reside naturally in cast or wrought Co-Cr-Mo alloys. The treated element should thereafter be dried by any suitable means such as by heating in an oven or by blowing the surface dry with a warm air stream.

Once the element has dried, it is allowed to cool to less than 30° C., e.g., to room temperature, prior to application of the silane coupling agent and the PMMA film thereto. Care should be taken that the clean surface not be contaminated during drying or cooling. In the case of prosthetic elements composed of Ti-6Al-4V or Co-Cr-Mo alloys, the prosthetic element should be given a final treatment in an alkaline bath, e.g., in a 1 N NaOH solution at 96° C. for one-half hour, prior to application of the silane coupling agent and the PMMA film and then cooled. Without the final alkaline bath just before application of the silane, the silane does not appear to bond to either the titanium or cobalt alloys.

The PMMA film is applied to the surface of the prosthetic element in the presence of a silane coupling agent. The silane coupling agent may either be mixed with the PMMA coating composition prior to application to the prosthetic element; or the prosthetic element may be treated with the silane coupling agent before application of the PMMA film. When admixed with the PMMA coating composition, the silane coupling agent is preferably used in an amount of about 0.01 to about 1.0 weight percent based on the weight of the PMMA. When used to treat the surface of a prosthetic element, the silane coupling agent is preferably in an aqueous solution comprising about 0.1 to about 1.0 percent by weight of the silane coupling agent; and the silane coupling agent is preferably prehydrolyzed, e.g., by the addition of an acid such as acetic acid. When used in admixture with the PMMA coating, it is preferred to wipe the surface of the prosthetic element with an alcohol, e.g., a mixture comprising 15% ethanol and 85% methanol after the coating procedure is finished in order to remove excess silane which diffuses to the coating surface where it may inhibit bone cement/coating interaction.

Silane coupling agents are organo-functional silane monomers that possess a dual reactivity. This property permits groups at one end of the molecule to hydrolyze to form silanols (Si-OH) which are able to condense with similar groups on glass or with metal oxides. At the other end of the silane molecule are organic groups which are able to react with an organic resin. The reaction mechanism of the resin with the silane in the case of thermosetting resins is specific to a given resin. It is generally accepted that the organo-functional group reacts with the thermosetting resins during cure. However, polymethylmethacrylate is a thermoplastic resin so that the mechanisms suggested above do not necessarily apply since thermoplastics are pre-polymerized before actual use. Thermoplastic resins demonstrate relative chemical inertness, It is postulated that chemical reaction takes place between the resin and the silane. This reaction can take several forms, namely, reaction with labile side groups or end groups on the polymer backbone, or reaction with polymer fragment radicals generated by chain scission of the polymer at molding temperature as well as by transesterification involving rupture of the polymer side chain.

Examples of silane coupling agents which may be used in the practice of this invention include N-beta-(aminoethyl)-gamma-aminopropyltrimethoxy silane, gamma-aminopropyltriethoxy silane, bis(beta-hydroxyethyl)-gamma-aminopropyltriethoxy silane, beta-(3,4-epoxycyclohexyl)ethyltrimethoxy silane, gamma-glycidoxypropyltrimethoxy silane, gamma-methacryloxypropyltrimethoxy silane, sulfonylazidosilanes, vinyl trichlorosilane, vinyltriethoxysilane, and vinyltris(beta-methoxyethyl) silane.

The PMMA film, either in admixture with the silane coupling agent or after treatment of the surface of the prosthetic element with the silane coupling agent, is applied to the prosthetic element by means of painting, spraying, dipping, powder coating, electrostatic coating, or in any other suitable manner in the form of a lacquer, powder or emulsion. The method and form utilized will depend on a number of various factors including the desired coating thickness, strength, implant geometry and surface roughness.

The film consists primarily of PMMA. However, other materials may be included in the film such as cross-linking agents, free radical catalysts, activators, plasticizers, chain transfer agents, inhibitors, plasticizing co-polymers, as well as adhesion promoters in the form of co-polymers, such as of acrylic acid and other freely orienting polar molecules.

One method of applying the film to the prosthetic element comprises the application of a PMMA lacquer to the element. Application may take the form of dipping, spraying, etc. A PMMA lacquer is prepared by dissolving PMMA high molecular weight beads in a solvent such as dichloromethane. A small amount of barium sulfate may be added to the lacquer in order to keep the coated surface from crazing as well as making the coating radio opaque. The concentration of polymer in the solution should be in the range of 0.01 g. per ml. to about 0.8 g. per ml., preferably from about 0.2 g. per ml. to about 0.4 g. ml., most preferably from about 0.25 g. per ml. to about 0.35 g. per ml.

The element is immersed in the lacquer for a period of time sufficient to form a suitable coating on the surface of the element. Such period of time may range from about 5 seconds to about 60 minutes, preferably from about 15 minutes to about 60 minutes, most preferably from about 25 to 35 minutes.

Another method of applying the film to the prosthetic element comprises the application of PMMA dissolved in methylmethacrylate. The MMA acts as a solvent for the PMMA and evaporates during the drying process. Weight ratios of PMMA:MMA ranging from 2:50 to 15:50 are preferred. Still another method of applying the PMMA coating is to coat the prosthetic element with MMA and catalyst. In cases where MMA is used, a high temperature curing step follows the coating to polymerize the MMA to PMMA. This may constitute the annealing step discussed hereinafter.

Upon completion of the application of PMMA to the element, the PMMA film is preferably annealed by exposing the coated element to a temperature above that of the glass transition temperature of PMMA, i.e., 70°–90° C., preferably from 80° C. to about 170° C., and most preferably about 160° C. The curing or annealing treatment insures complete polymerization and removal of any volatile components from the film. High pressures, i.e., greater than 100 psi may be applied to inhibit bubble formation. Moreover, by heating the film to a temperature above the glass transition temperature of PMMA, any mechanical stresses in the film developed during the drying thereof will be eliminated.

The rate at which the coated element is cooled following the annealing treatment is preferably controlled to insure that it does not exceed about 1.5° C. per minute until the coated element reaches a temperature of about 80° C. This insures that only minimal stresses are formed in the film during cooling. If desired, the film may be crosslinked by chemical and/or radiation techniques.

The thickness of the film thus produced is not of critical importance; however, the preferred minimum thickness of the film should be about 0.0001 inch, more preferably about 0.001 inch, most preferably about 0.002 inch.

Upon completion of the annealing or curing of the PMMA film, the coated prosthetic element is ready for use as a prosthesis. If the prothesis is a bone implant prosthesis, the interior of the bone is removed and cleaned and a PMMA bone cement is applied to the interior of the bone. Thereafter, the implant portion of the prostheses, coated in accordance with the present invention is inserted into the interior of the bone. If desired, the coating may be softened with a solvent such as MMA monomer prior to insertion into the bone. This causes the PMMA film to swell and soften, thus allowing for greater mechanical and chemical interaction between the coating and bone cement.

Figure 2:
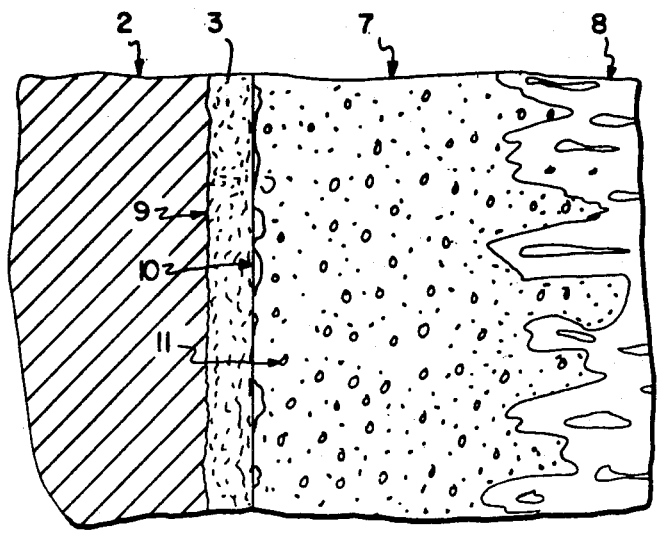
FIG. 2 illustrates an enlarged fragmentary view of a PMMA coated bone implant, as shown in FIG. 1, which has been fixedly adhered to the interior of a bone by means of a PMMA bone cement.

In FIG. 2, an enlarged fragmentary view of a coated prostheses which has been fixedly adhered to bone by means of a PMMA bone cement is illustrated. Prosthetic element 2 is connected to bone cement 7 via the PMMA film 3. Bone 8 is shown to be adhered to the bone cement. The interface 9 between the PMMA film and the element is free of defects and any weak boundary layer due to the precoating treatment of the element. The interface 10 between the PMMA coating and bone cement 7, represents both a chemical and mechanical adherence. Flaws 11 in the bone cement 7 are displaced away from the interface 9 due to the thickness of the film 3.

When a PMMA coating is applied to a prosthetic element in accordance with the practice of this invention, there results an improved adhesion between the surface of the prosthetic element and the PMMA film as compared to a coating in which the silane coupling agent is omitted. The adhesive bonds thus created are resistant to prolonged exposure to 37° C. saline solution. The PMMA film effectively protects the surface of the prosthetic element from pre-implantation contamination. Upon implantation the bone-cement comes in contact with the PMMA film. The unreacted monomer in the bone-cement softens the surface of the film permitting some entanglement of the polymer chains, effectively creating some level of covalent bonding between the bone-cement and the PMMA film. Hence, an ideal interface is formed in spite of the significant clinical restrictions.

The following examples illustrate the pre-coating procedures for three different metal alloys. In each of these examples, the silane coupling agent solution was prepared by preparing a 0.5% by volume aqueous solution of gamma-methacryloxypropyltrimethoxy silane and hydrolyzing this solution by the addition of 0.25 ml. of 1 N acetic acid to every 50 ml. of aqueous solution. The solution was allowed to stand for one hour after which the metal samples were placed in the solution for one hour whereupon they were removed and dried in an oven at 90° C. for one-half hour. After cooling in air for one-half hour, the metal samples were coated with a PMMA film by dipping them in a solution comprising three gms. of PMMA dissolved in 10 ml. of MMA. Subsequently, the coatings were dried for two hours at 80° C. and then cured at 160° C. for 24 hours in an oven. The oven was then turned off and allowed to cool to room temperature.

EXAMPLE 1

A cobalt-chromium-molybdenum alloy prosthetic element sample is treated as follows: The surface is sand blasted in order to provide an approximately 1.0 m roughness. The sample is then degreased in boiling 1 N sodium hydroxide solution for 15 minutes and rinsed in distilled water for 10 seconds. The surface is acid etched in a 75% by volume aqueous solution of sulfuric acid at 100° to 120° C. The etching process results in black "smut" composed principally of carbon. Etching is continued for 30 seconds and the sample is then rinsed in distilled water for approximately 10 seconds. The sample is then desmutted and passivated simultaneously by immersing it in an aqueous solution comprising 35% by volume of nitric acid and 5% by volume of hydrofluoric acid at room temperature for 30 minutes. The sample is rinsed in distilled water for 10 seconds. It is then placed in boiling 1 N sodium hydroxide solution for 15 minutes. It is then rinsed and cooled in distilled water. Care is taken to minimize the length of time the sample is in the water to that necessary to reduce the sample temperature to just less than 30° C. This step is carried out in an ultrasonic cleaner in order to completely remove weakly attached carbides. The sample is placed in the silane solution previously described for a duration of 30 minutes. The sample is then removed from the silane solution and without rinsing is placed into a gravity oven at 90° C. for 15 minutes. It is then cooled to approximately 30° C. and coated as previously described. The resultant coated sample is resistant to prolonged exposure to 37° C. saline solution.

EXAMPLE 2

A Ti-6Al-4V alloy prosthetic element sample is provided and treated as follows: The surface is sand blasted in order to provide a roughness of approximately 2.0 μm. The element is then boiled in 1 N sodium hydroxide for 15 minutes, rinsed and cooled in distilled water. The time required to reduce the sample temperature to less than 30° is minimized since prolonged exposure to water appears to diminish the potential for silane-surface interaction. The sample is immersed in the aqueous silane solution previously described for 30 minutes and is then dried in air at 90° for 15 minutes. The sample is then cooled to less than 30° C. and coated as previously described. The resultant PMMA coated sample is resistant to prolonged exposure to 37° C. saline solution.

EXAMPLE 3

A stainless steel, i.e., SS316LVM, prosthetic element sample is treated according to the ASTM standard procedure for the preparation of stainless steel for adhesion (ASTM-D2651-79). This procedure, including the added silane pre-treatment is as follows: The surface of the sample is sand blasted in order to provide a surface roughness of approximately 2 μm. It is degreased in boiling 1 N sodium hydroxide solution for 10 minutes and rinsed for 10 seconds in distilled water. This is followed by an acid-etch in aqueous solution composed of 30% by volume of sulfuric acid at between 65.5° and 71.1° C. for 10 seconds after vigorous etching begins. The sample is then rinsed for 10 seconds in distilled water and passivated in an aqueous solution of 12% by volume of nitric acid at 45° C. for 10 minutes. The sample is then immersed in the aqueous silane solution previously described for 30 minutes and dried at 90° C. for 15 minutes. Finally, the sample is cooled to room temperature and coated as previously described.

I claim:

1. In a process for fixedly adhering a polymethylmethacrylate film to a prosthetic element to provide an improved prosthesis adapted to be joined to bone by means of bone cement, said prosthesis having been prepared by the steps of treating said prosthetic element to eliminate any weak boundary layer, applying polymethylmethacrylate to said treated surface to form a film thereon; and thereafter annealing said polymethylmethacrylate film, the improvement which comprises applying polymethylmethacrylate to the surface of said prosthetic element in the presence of a silane coupling agent.

2. A process as defined in claim 1 wherein said prosthetic element is composed of metal.

3. A process as defined in claim 2 wherein said element is cooled to less than 30° C. prior to application of the silane coupling agent and PMMA film thereto.

4. A process as defined in claim 3 wherein said prosthetic element is treated in an alkaline bath and then cooled to less than 30° C. immediately prior to applying said silane coupling agent.

5. A process as defined in claim 4 wherein said metal is a cobalt-chromium-molybdenum alloy.

6. A process as defined in claim 4 wherein said metal is a titanium alloy.

7. A process as defined in claim 3 wherein said metal is stainless steel.

8. A process as defined in claim 3 wherein said silane coupling agent is admixed with said polymethylmethacrylate prior to application to said surface.

9. A process as defined in claim 3 wherein said surface is treated with said silane coupling agent prior to application of said polymethylmethacrylate.

10. A process as defined in claim 3 wherein said silane coupling agent is gamma-methacryloxypropyltrimethoxysilane.

11. A prosthesis obtained by the process of claim 1.
12. A prosthesis obtained by the process of claim 2.
13. A prosthesis obtained by the process of claim 3.
14. A prosthesis obtained by the process of claim 4.
15. A prosthesis obtained by the process of claim 5.
16. A prosthesis obtained by the process of claim 6.
17. A prosthesis obtained by the process of claim 7.
18. A prosthesis obtained by the process of claim 8.
19. A prosthesis obtained by the process of claim 9.
20. A prosthesis obtained by the process of claim 10.

21. A process comprising joining a prosthesis as defined in claim 11 to bone by contacting said bone and the polymethylmethacrylate film adhered to said prosthesis with bone cement.

22. A process comprising joining a prosthesis as defined in claim 12 to bone by contacting said bone and the polymethylmethacrylate film adhered to said prosthesis with bone cement.

23. A process comprising joining a prosthesis as defined in claim 13 to bone by contacting said bone and the polymethylmethacrylate film adhered to said prosthesis with bone cement.

24. A process comprising joining a prosthesis as defined in claim 14 to bone by contacting said bone and the polymethylmethacrylate film adhered to said prosthesis with bone cement.

25. A process comprising joining a prosthesis as defined in claim 15 to bone by contacting said bone and the polymethylmethacrylate film adhered to said prosthesis with bone cement.

26. A process comprising joining a prosthesis as defined in claim 16 to bone by contacting said bone and the polymethylmethacrylate film adhered to said prosthesis with bone cement.

27. A process comprising joining a prosthesis as defined in claim 17 to bone by contacting said bone and the polymethylmethacrylate film adhered to said prosthesis with bone cement.

28. A process comprising joining a prosthesis as defined in claim 18 to bone by contacting said bone and the polymethylmethacrylate film adhered to said prosthesis with bone cement.

29. A process comprising joining a prosthesis as defined in claim 19 to bone by contacting said bone and the polymethylmethacrylate film adhered to said prosthesis with bone cement.

30. A process comprising joining a prosthesis as defined in claim 20 to bone by contacting said bone and the polymethylmethacrylate film adhered to said prosthesis with bone cement.

* * * * *